United States Patent [19]

Urry

[11] Patent Number: 5,520,672
[45] Date of Patent: May 28, 1996

[54] SUPERABSORBENT MATERIALS AND USES THEREOF

[76] Inventor: Dan W. Urry, 2423 Vestavia Dr., Birmingham, Ala. 35216

[21] Appl. No.: 384,566

[22] Filed: Feb. 6, 1995

Related U.S. Application Data

[62] Division of Ser. No. 688,185, Apr. 19, 1991, Pat. No. 5,393,602.

[51] Int. Cl.⁶ ........................................................ B32B 9/00
[52] U.S. Cl. ............................ 604/368; 604/358; 604/367
[58] Field of Search .................................... 604/368, 367, 604/358

[56] References Cited

U.S. PATENT DOCUMENTS

| | | | |
|---|---|---|---|
| 4,474,851 | 10/1984 | Urry | 428/373 |
| 4,895,896 | 1/1990 | Muller-Lierheim | 525/54.1 |
| 5,250,516 | 10/1993 | Urry | 514/17 |
| 5,393,602 | 2/1995 | Urry | 428/290 |

FOREIGN PATENT DOCUMENTS

WO89/10099  11/1989  WIPO.

OTHER PUBLICATIONS

Urry, D. W., "Entropic Elastic Processes in Protein Mechansims. I. Elastic Structure Due to an Inverse Temperature Transition and Elasticity Due to Internal Chain Dynamics" (1988) *Journal of Protein Chemistry* 7(1):1–34.

Urry, D. W., "Entropic Elstic Processes in Protein Mechanisms. II. Simple (Passive) and Coupled (Active) Development of Elastic Forces" (1988) *Journal of Protein Chemistry* 7(2):81–114.

Urry, D. W., "General Properties and Applications of Sequential Polypeptides from Elastin and Their Analogs" (1990) *Am. Chem. Soc., Div. of Poly. Mat.: Sci. & Eng.* 62:587–593.

Hollinger et al., "A synthetic Polypentapeptide of Elastin for Initiating Calcification" (1988) *Calcif Tissue Int* 42:321–236.

Urry, D. W., "Free Energy (Chemomechanical) Transduction in Elastomeric Polypeptides by Chemical Potential Modulaton of an Inverse Temperature Transition" (1988) *International Journal of Quantum Chemistry: Quantum Biology symposium* 15:235–245.

Edsall, J. T. and McKenzie, H. A., "Water and Proteins. II. The Location and Dynamics of Water in Protein Systems and Its Relation to Their Stability and Properties" (1983) *Adv. Biophys.* 16"53–183.

Kauzmann, W., "Some Factors in the Interpretation of Protein Denaturation" (1959) *Adv. Protein Chem.* 14:1–63.

Urry et al., "Aqueous Interfacial Driving Forces in the Folding and Assembly of Protein (Elastin)–Based Polyers: Differential Scanning Calorimetry Studies" (1990) *Poly. Preprint Am. Chem. Soc. Div. Polym Chem.* pp. 188–189.

Urry, D. W., "Protein Elasticity Based on Conformations of Sequential Polypeptides: The Biological Elastic Fiber" (1984) *Journal of Protein Chemistry* 3(5/6):403–435.

(List continued on next page.)

*Primary Examiner*—James J. Bell
*Attorney, Agent, or Firm*—Cooley Godward Castro Huddleson and Tatum

[57] ABSTRACT

Polymeric materials having an inverse temperature transition, particularly bioelastic polymers comprising monomeric units selected from the group consisting of bioelastic pentapeptides, tetrapeptides, and nonapeptides, have been found to have controllable absorbent properties that can be varied with temperature or contact with liquids. The materials are selected to be in a contracted or swollen state initially, depending on the specific use. When the material is located under different conditions (such as a different temperature resulting from being either in contact with or at distance from human skin), the material undergoes swelling or contraction to switch to the other state.

15 Claims, 4 Drawing Sheets

OTHER PUBLICATIONS

Chang et al., "Nuclear Overhauser Effect and Computational Characterization of the β–Spiral of the Polypentapeptide of Elastin" (1989) *Journal of Biomolecular Structure & Dynamics*, ISSN 0739–1102 6(5):851–858.

Chang, D. K. and Urry, D. W., "Polypentapeptide of Elastin: Damping of Internal Chain Dynamics on Extension" (1989)*Journal of Computational Chemistry* 10(6):850–855.

Urry et al., "Mechanochemical coupling in synthetic polypeptides by modulation of an inverse temperature transition" (1988) *Proc. Natl. Acad. Sci.* USA 85:3407–3411.

Urry et al., "A New Mechanism of Mechanochemical Coupling: Stretch–Induced Increase in Carboxyl $pK_a$ as a Diagnostic" (1990) *Biopolymers* 30:215–218.

Urry et al., "pK Shift of Functional Group in Mechanochemical Coupling Due to Hydrophobic Effect: Evidence for an apolar–polar repulsion free energy in water" (1988) *Biochemical and Biophysical Research Communications* 153(2):832–839.

Robinson, A. B., "Evolution and the Distribution of Glutaminyl and Asparaginyl Residues in Proteins" (1974) *Proc. Nat. Acad. Sci. USA* 71(3):885–888.

Urry et al., "The Poly(Nonapeptide) of Elastin: A New Elastomeric Polypeptide Biomaterial" (1990) *Progress in Biomedical Polymers* pp. 171–178.

Urry et al., "Poly($VAL^1$–$PRO^2$–$ALA^3$–$VAL^4GLY^5$): A Reversible Inverse Thermoplastic" (1991) *Biotechnology and Polymers* pp. 265–274.

Urry et al., "Chemical Potential Driven Contraction and Relaxation by Ionic Strength Modulation of an Inverse Temperature Transition" (1988) *J. Am. Chem. Soc.* 110(10):3303–3305.

Sciortino et al., "Nucleation and Accretion of Bioelastomeric Fibers at Biological Temperatures and Low Concentrations" (1988) *Biochemical and Biophysical Research Communications* 157(3):1061–1066.

Sciortino et al., "Self–Assembly of a Bioelastomeric Structure: Solution Dynamics and the Spinodal and coacervation Lines" (1990) *Biopolymers* 29:1401–1407.

SUPERABSORBENT MATERIALS AND USES THEREOF

CROSS REFERENCE TO RELATED APPLICATIONS

This application is a Divisional of U.S. application Ser. No. 07/688,185, filed Apr. 19, 1991 now U.S. Pat. No. 5,393,602.

TECHNICAL FIELD

The present invention is directed to the field of absorbent material and to uses thereof.

BACKGROUND

Materials capable of absorbing liquids, particularly aqueous liquids, are employed in numerous everyday uses, such as in the manufacture of towels (cloth or paper) and various specialty absorbing materials, such as diapers and other absorbent garments, wound dressings, medical sponges, tissues, napkins, liners, toilet paper, tampons, sanitary napkins, towelettes, and cleaning wipes. Other commonly used absorbents include aerosol absorbents such as antiperspirants, and bulk liquid absorbents, which are often in the form of powders and are frequently used to absorb large spills on surfaces. These materials have traditionally been prepared from cloth or paper, but recent developments have resulted in a number of absorbent material of different structure, such as hydrogels and hydroxymethylmethacrlyate. See, for example, U.S. Pat. Nos. 4,935,022; and 4,685,909. Absorbent materials have previously been prepared from cellulosic fibers, blown microfibers, staple fibers, ion exchange fibers, and conjugate fibers of different melting points. See for example, U.S. Pat. Nos. 4,851,284; 4,818,598; and 4,865,596. In addition, web structures prepared from entangled hydrophilic nylon microfibers which contain staple fibers and/or particles of hydrogel-forming polymeric gelling agent are described in U.S. Pat. No. 4,923,454. There exists a continual need to provide optimum functional properties of absorbency at moderate costs.

Bioelastic polypeptides are a relatively new development that arose in the laboratories of the present inventor and which are disclosed in a series of previously filed patents and patent applications. For example, U.S. Pat. No. 4,474,851 describes a number of tetrapeptide and pentapeptide repeating units that can be used to form a bioelastic polymer. Specific bioelastic polymers are also described in U.S. Pat. Nos. 4,132,746; 4,187,852; 4,500,700; 4,589,882; and 4,870,055. Bioelastic polymers are also disclosed in related patents directed to polymers containing peptide repeating units that are prepared for other purposes but which can also contain bioelastic segments in the final polymer; see U.S. Pat. No. 4,605,413. A number of other bioelastic materials and methods for their use are described in pending U.S. patent applications including the following: "Stimulation of Chemotaxis by Chemotactic Peptides," U.S. Ser. No. 355,090, filed May 16, 1989; "Bioelastomer Containing Tetra/Pentapeptide Units," U.S. Ser. No. 062,557, filed Jun. 15, 1987; "Reversible Mechanochemical Engines Comprised of Bioelastomers," U.S. Ser. No. 410,018, filed Sep. 20, 1989; "Bioelastomeric Materials Suitable for the Protection of Wound Repair Sites," U.S. Ser. No. 184,407, filed Apr. 21, 1988; "Elastomeric Polypeptides as Vascular Prosthetic Materials," U.S. Ser. No. 184,873, filed Apr. 22, 1988; and "Polynonapeptide Bioelastomers having an Increased Elastic Modulus," U.S. Ser. No. 314,115, filed Feb. 23, 1989. All of these patents and patent applications are herein incorporated by reference, as they describe in detail bioelastomers that can be used in the compositions and methods of the present invention. These bioelastic materials have been proposed for a number of uses, as indicated by the general subject matter of the applications and patents as set forth above.

The present invention is directed to a new use of bioelastic materials, namely as an absorbent, either alone or in combination with previously known absorbents and structural materials. It has been discovered that bioelastic materials have a number of properties, including but not limited to controllable absorbency, that make them ideal for use in a number of situations that require high levels of absorbency.

RELEVANT LITERATURE

In addition to the patents and patent applications cited above, a number of publications in the scientific literature are relevant to the present invention. These publications are listed below, and reference is made in the following specification to these literature references by giving the reference number in parentheses at the location where the reference is being cited.

1. Urry, D. W.: *J. Protein Chem.* 7, 1–34 (1988).
2. Urry, D. W.: *J. Protein Chem.* 7, 81–114 (1989).
3. Urry, D. W.: *American Chemical Society, Div. of Polymeric Materials: Sci. and Engineering* 62 (1990).
4. Hollinger, J. O., J. P. Schmitz, R. Yaskovich, M. M. Long, K. U. Prasad, and D. W. Urry: *Calacif. Tissue Int.* 42, 231–236 (1988)
5. Urry, D. W.: *Intl. J. Quantum Chem.: Quantum Biol. Symp.* 15, 235–245 (1988).
6. Edsall, J. T. and H. A. McKenzie: *Adv. Biophys.* 16, 53–183 (1983).
7. Kauzman, W.: *Adv. Protein Chem.* 14, 1–63 (1959).
8. Urry, D. W., C-H Luan, R. Dean Harris, and Karl U. Prasad: *Polymer Preprint Am. Chem. Soc. Div. Polym. Chem.* (1990).
9. Urry, D. W.: *J. Protein Chem.* 3, 403–436 (1984).
10. Chang, D. K., C. M. Venkatachalam, K. U. Prasad, and D. W. Urry; *J. of Biomolecular Structure & Dynamics* 6, 851–858 (1989).
11. Chang, D. K. and D. W. Urry: *J. of Computational Chemistry* 10, 850–855 (1989).
12. Urry, D. W., B. Haynes, H. Zhang, R. D. Harris, and K. U. Prasad: *Proc. Natl. Acad. Sci. USA* 85, 3407–3411 (1988).
13. Urry, D. W., Shao Qing Peng, Larry Hayes, John Jaggard, and R. Dean Harris: *Biopolymers* (1990).
14. Urry, D. W., D. K. Chang, H. Zhang, and K. U. Prasad: *Biochem. Biophys. Res. Commun.* 153, 832–839 (1988).
15. Robinson, A. B.: *Proc. Nat. Acad. Sci. USA* 71, 885–888 (1974).
16. Urry, D. W.: In *Methods in Enzymology*, (L. W. Cunningham and D. W. Frederiksen, Eds.) Academic Press, Inc. 82, 673–716 (1982).
17. Urry, D. W., John Jaggard, R. D. Harris, D. K. Chang, and K. U. Prasad: In *Progress in Biomedical Polymers* (Charles G. Gebelein and Richard L. Dunn, Eds.), Plenum Publishing Co. (1990).
18. Urry, D. W., J. Jaggard, K. U. Prasad, T. Parker, and R. D. Harris: Plenum Press (1990).
19. Urry, D. W., R. D. Harris, and K. U. Prasad: *J. Am. Chem. Soc.* 110, 3303–3305 (1988).
20. Sciortino, F., M. U. Palma, D. W. Urry, and K. U. Prasad: *Biochem. Biophys. Res. Commun.* 157, 1061–1066 (1988).

21. Sciortino, F., D. W. Urry, M. U. Palma, and K. U. Prasad: *Biopolymers* (1990).

SUMMARY OF THE INVENTION

It is an object of the present invention to provide an absorbent that will have different absorbencies under different conditions, such as different temperatures, salt concentrations, pressures, and pH.

It is a further object of this invention to provide an absorbent that will have relatively low absorbent, wicking properties when at a higher temperature and increased absorbency at lower temperatures.

It is still another object of the invention to provide a shape-stable absorbent that will readily absorb and retain aqueous solutions when under external pressure that would normally compress the absorbent and expel the liquid.

These and other objects of the present invention as will hereinafter become more readily apparent have been accomplished by providing a method of absorbing aqueous liquids, which comprises contacting said liquid with a polymer showing an inverse temperature transition in the range of liquid water. Preferred polymers comprise elastomeric units selected from the group consisting of bioelastic pentapeptides, tetrapeptides, and nonapeptides. By selecting the side chains present in the polymer portion of the composition, fine control is possible over the absorbence properties of the composition including the ability of the absorbent to retain absorbed liquid under stresses and external pressures. In particularly preferred embodiments, the invention contemplates diapers, other absorbent garments, and hygienic devices which directly contact the user, antiperspirants, wound dressings, appliance or machine coatings such as a coating for a water roll of an offset printer, and other absorbents in which the properties of the bioelastomers are selected to wick liquids away from a warmer region into cooler regions of the absorbent that are removed from the point of higher temperature. Controllable polymers are also provided that resist pressure-driven expulsion of liquids (such as by sitting on a diaper or applying pressure to a damp paper towel), as they tend to expand under external pressure. Thus, the present invention is particularly useful in preventing leakage around constricted edges at the thigh or waist of diapers, incontinent devices and the like, as well as pressure-sensitive bandages, sanitary dressings, and as a coating on pressure rollers, such as those used in painting and printing.

DESCRIPTION OF THE DRAWINGS

The present invention will be better understood by reference to the following detailed description of the invention and the drawings which form part of the present specification, wherein.

DESCRIPTION OF THE SPECIFIC EMBODIMENTS

Figure 1:
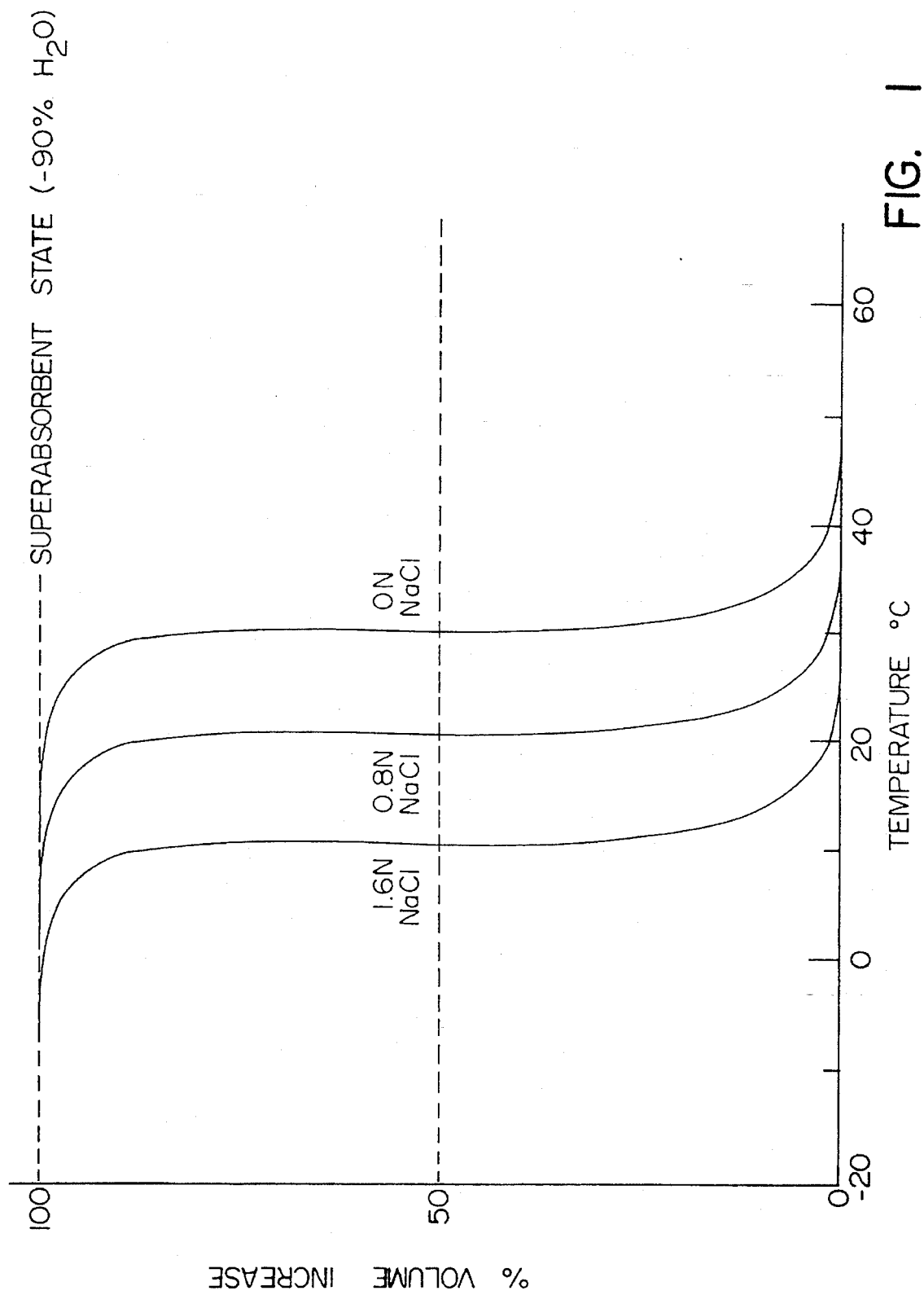
FIG. 1 is a graph showing modulation of inverse temperature transitions with different solvents (aqueous salt concentrations).

The present invention provides new uses for and new compositions containing bioelastic polypeptides as well as other polymers that have an inverse temperature transition. Bioelastic polypeptides have been previously characterized and described in a number of patents and patent applications described above. These preferred materials contain either tetrapeptide, pentapeptide, or nonapeptide monomers which individually act as elastomeric units within the total polypeptide containing the monomeric units. The elasticity of the monomeric units is believed to be due to a series of β-turns in the protein's secondary structure, i.e., the conformation of its peptide chain, separated by dynamic (as opposed to rigid) bridging segments suspended between the β-turns. A β-turn is characterized by a 10-atom hydrogen-bonded ring of the following formula:

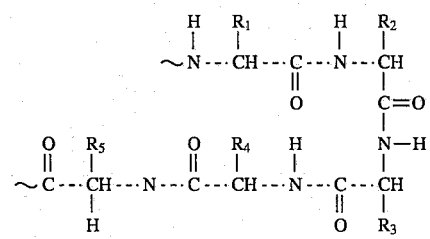

In this formula $R_1$–$R_5$ represent the side groups of the respective amino acid residues. The 10-atom ring consists of the carbonyl oxygen of the first amino acid, the amino hydrogen of the fourth amino acid, and the intervening backbone atoms of amino acids two and three. In this monomeric unit as shown, the remaining backbone atoms of the chain (the remainder of amino acid four, amino acid five, and the first part of amino acid one of the next pentameric unit) form the bridging segment that is suspended between adjacent β-turns. As indicated by the existence of both tetrapeptide and nonapeptide elastomeric repeating units, the length of the bridging segment can vary to accommodate the absence of amino acid 5 or the presence of amino acids 6–9.

This β-turn-containing structure is described in the prior patents and patent applications cited above and need not be described again in detail. Considerable variation in the amino acids that are present at various locations in the repeating units is possible as long as the multiple β-turns with intervening suspended bridging segments are retained in order to preserve elasticity. Furthermore, it is possible to prepare polypeptides in which these monomeric units are interspersed throughout a larger polypeptide that contains peptide segments designed for other purposes. For example, rigid segments can be included to increase the modulus of elasticity or segments having biological activity (such as chemotaxis and cell attachment) can be included for their biological activity.

These elastomeric materials, which include the prototypic poly($Val^1$-$Pro^2$-$Gly^3$-$Val^4$-$Gly^5$) and poly($Val^1$-$Pro^2$-$Gly^3$-$Gly^4$) molecules as well as numerous analogues, when combined with water form viscoelastic phases which when cross-linked result in soft, compliant, elastomeric matrices (1–3). The VPGVG-based polypentapeptide (and other bioelastomers) has been shown to be biocompatible both before and after cross-linking (4). As implants, such bioelastic polymers are biodegradable, leading to the release of products natural to the body, such as short peptide chains and free amino acids. These polymers, also referred to as elastomeric polypeptide biomaterials or simply bioelastic materials, can be prepared with widely different water compositions, with a wide range of hydrophobicities, with almost any desired shape and porosity, and with a variable degree of cross-linking (either chemically or by irradiation) by selecting different amino acids for the different positions of the monomeric units and by varying the cross-linking process used to form the final product.

The present invention arose in part with the realization that these polymeric materials have a number of properties, generally arising from their inverse temperature transitions, that make them ideal for use in a variety of environments requiring absorbence of aqueous fluids. It is emphasized here that the results of balancing hydrophobic (apolar) and polar moieties so that a material will have an inverse temperature transition are not unique to polypeptides but will be applicable to any polymers wherever the appropriate balance can be achieved, for example, for polyesters, polyamides, poly(organophosphazenes), polyacrylamides, polyacrylates, polymethacrylamides, polymethacrylates, etc. Using the relative hydrophobicities and sizes of the side chains, it is possible to construct polymers which will exhibit inverse temperature transitions by a systematic, knowledge-based approach. This approach can be used with natural compounds such as the poly β-hydroxy alkanoates where there is stereochemical regularity. This can, of course, be achieved with polymers that are degradable as well as with polymers that are not so degradable and also with polymers having greater thermal stability.

The phenomena of inverse temperature transitions in aqueous systems is general and occurs in a number of amphiphilic systems, commonly polymers, that have an appropriate balance and arrangement of apolar and polar moieties. The polar species contribute to the solubility in water at low temperature, a solubility that results in waters of hydrophobic hydration for the apolar moieties. The waters of hydrophobic hydration, often referred to as clathrate or clathrate-like water, have specific thermodynamic properties: an exothermic heat of hydration (a negative $\Delta H$) and a negative entropy of hydration (6, 7). On raising the temperature, by means of an endothermic transition (8), the low entropy waters of hydrophobic hydration become bulk water with a significant increase in solvent entropy as the polymers fold and aggregate, optimizing intra- and intermolecular contacts between hydrophobic (apolar) moieties with a somewhat lesser decrease in polymer entropy than increase in solvent entropy. Such polymers, when their transitions occur between 0° and 100° C., can be used to control events in the aqueous environments that occur in biology.

SUPERABSORBENT MATERIALS BASED ON THE PHENOMENA OF INVERSE TEMPERATURE TRANSITION

The choice of absorption material or absorption core in diapers, sanitary napkins, incontinence products and the like is made with regard to both the actual functional properties of absorbency and the economic costs. The term "absorbing functional property" refers to the balance between the absorbent material utilized or required to absorb and retain a specific quantity of fluid. The functional properties of absorbency also encompass the capacity of co-action with other materials in the finished product such as the outer layer of material facing the user of the product so as to obtain a dry surface which remains dry even after a relatively long period of use.

The present invention's polymeric systems with the correct balance of hydrophobic (apolar) and polar residues can be soluble in water at low temperatures but, as the temperature is raised through a transitional range, they aggregate into condensed, more-ordered states. That is, they exhibit a phase transition from a state I (the solution) to a state II (a condensed phase) which is more dense and which is in equilibrium with the overlying solution. When such polymeric systems are cross-linked, they are seen to swell to the extents allowed by the cross-linking on lowering the temperature below the transition and to contract with the expulsion of water on raising the temperature above the transitional temperature range. Most systems (a common example would be crystals in equilibrium with a mother liquor), become more soluble and less ordered on raising the temperature. In contrast, the phenomenon described in the present invention is called an inverse temperature transition where the molecular basis for such a transition resides in the nature of the hydration shell that surrounds hydrophobic (apolar) moieties.

Dissolution of hydrophobic moieties in water is an exothermic process ($\Delta H$ is negative) but the solubility, which depends on a negative Gibbs free energy of hydration ($\Delta G(\text{hydration}) = \Delta H - T\Delta S$) of hydrophobic moieties, is generally low because of a significant negative entropy change ($\Delta S$) as water molecules in bulk solution become more ordered in the shell of water surrounding the hydrophobic moieties. Therefore, even though raising the temperature of certain polymers dissolved in water can cause them to assemble into a lower entropy condensed phase, the more-ordered waters of hydrophobic hydration surrounding the hydrophobic moieties of the polymer in its dissolved state become less-ordered bulk water as the polymers aggregate. The net result on raising the temperature through the transition is an increase in disorder, i.e. an increase in entropy, for the system as a whole in keeping with the second law of thermodynamics, but importantly there has occurred a very useful increase in order, decrease in entropy, for the polymeric part of the system.

In the low temperature state (state I) the cross-linked polymer is a hydrogel or a superabsorbent which expels substantial amounts of water when the temperature is raised to become the more-dense, condensed phase (state II). There are many ways in which the temperature of transition can be shifted. This means it becomes possible without a change in temperature to shift from state I to state II or vice a versa. The phase transition can be used to carry out work (e.g. for the state I → state II transition, the cross-linked matrix contracts and can lift weights that are a thousand of times greater than the dry weight of the cross-linked matrix). Thus the inverse temperature transition itself is a thermally driven contraction, that is, such materials exhibit thermochemical transduction.

If the system is in state I at ambient temperature, for example, and a chemical concentration change causes a lowering of the transition temperature to below ambient temperature, then the chemical concentration change will drive contraction as the system shifts to state II. This is chemomechanical transduction and it can be achieved by two different general chemical processes, a polymer-based process and a solvent-based process.

The polymer-based process utilizes functional side chains in the polymer which, for example by protonation or deprotonation (i.e. pH change) can be shifted between more polar (less hydrophobic) and less polar (more hydrophobic) states. In the solvent-based process, changes in composition of the solvent can change the temperature of the transition. For example, increasing the concentration of salt (NaCl) lowers the transition temperature; adding urea (from urine for example) raises the transition temperature; adding ethylene glycol lowers the transition temperature and so forth. An example of the changes in the transition temperature with change in salt content of the aqueous medium is shown in FIG. 1. It also has been recently shown in applicant's application filed on even date with the present application Ser. No. 07/688,324, filed Apr. 22, 1991 now U.S. Pat. No. 5,226,292 that a change in pressure can shift the transition temperature and can result in baromechanical transduction.

Polymeric systems designed in accordance with the present invention can be used for a variety of functions with a desired transition temperature. With knowledge of the effect of the solutes involved in a particular application, the transition temperature can be designed for that purpose. For example, a preferred embodiment is one of absorbing bodily fluids, specifically a diaper application. In this embodiment it is possible to utilize the thermal gradients from body surface temperature to ambient temperature that naturally occur in a diaper or incontinence appliance or apparel in combination with appropriately designed polymeric materials that would wick aqueous fluids from warmer to cooler temperatures. In this fashion, the temperature of the inverse temperature transition can be adjusted as desired from 0° C. to 70° C. but specifically between body surface temperature and ambient temperature. Furthermore, as the suitably cross-linked matrices exhibit shape memory, the diaper can be properly shaped and sized such that, when wet, it would appropriately conform to body contours. The effect of pressure, as noted above, shifts the transition toward state I, the superabsorbent state, such that the effect of sitting on the diaper would have a component of increased absorbency, thereby decreasing the tendency to squeeze fluid and contents out of the diaper.

It may be advantageous in some circumstances to combine the absorbent of the present invention with other absorbent agents or to coat or otherwise compound cellulose or other suitable material with the transducible absorbent of the invention in order to provide a superabsorbent capable of undergoing an inverse temperature transition, with the possibilities inherent in that property, on a cellulose or other support or surface. One advantage is to have a biodegradable superabsorbent in accordance with the present invention, which would solve waste disposal problems found in disposable diapers. Biodegradability would include the capacity to have chemical linkages which could be sufficiently and selectively destabilized so that the filler of a diaper, sanitary pad or tampon could decompose at a rate sufficient to be flushable. This process could include the use of added enzymes, such as thermolysin, to the toilet bowl or other chemicals coated to the inside of a pouch in which the absorbent product could be disposed. See Ser. No. 07/499,697, filed Mar. 27, 1990, for a discussion of biodegradiation of bioelastomers. Reusable diapers, however, are also contemplated by the present invention.

Thus, the present invention has numerous applications in wound dressings, bandages, medical patches to deliver drugs, and other products which contact the users skin or body surface. Veterinarian applications are contemplated by the subject invention, as well as uses in absorbing spill clean-ups, and liquid distribution systems where selected temperatures can be utilized to wick liquid to layers or surfaces as desired.

A related although apparently different use of the materials of the invention is as structural polymers from which to form soft contact lenses. Such lenses are currently prepared highly absorbent polymeric materials. A particularly useful material for contact lenses is poly(VPGVG), which is described in detail above and in the referenced patents and patent applications. This polymer has the same density and refractive index as the lens of the human eye and has the superabsorbency properties required of good contact lenses. In addition, poly(VPGVG) is very biocompatible and shows no tendency to cause formation of the protein coatings on its surface that are the bane of contact-lens wearers. Biological implants of this material have previously been shown not to cause fibrous encapsulation to occur when implanted in a living system. The contact lens can be prepared in the same manner as now used for other materials, merely substituting the polymer of the invention for the previously used structural polymer.

CONTROL OF INVERSE TEMPERATURE TRANSITION IN BIOELASTOMERS AND USE IN DESIGNING ABSORBENTS

A description of the process of designing bioelastomers specifically for use as selective absorbents is described below in detail. Basically, a bioelastomer is selected that is capable of changing from a condensed to a swollen state upon contact with a pre-selected physiological condition (such as temperature or salt content) so that the inverse temperature transition point of the bioelastomer is selectively located either above or below the ambient temperature of the local environment in which the bioelastomer is found; this allows selective unfolding and disassembly of polymer matrices to favor absorbency or brings about a contraction that causes the hydrophobic properties of the elastomers to take precedence.

The specific examples used below to illustrate this process are mostly examples of elastomeric polypentapeptide matrices. However, it will be apparent that the same considerations can be applied to elastomeric tetrapeptide and nonapeptide matrices and to matrices prepared using these elastomeric units in combination with other polypeptide units as described previously for bioelastic materials used in other circumstances.

The phenomena of inverse temperature transitions in aqueous systems is general and occurs in a number of amphiphilic systems, commonly polymers, that have an appropriate balance and arrangement of apolar and polar moieties. The polar species contribute to the solubility in water at low temperature, a solubility that results in waters of hydrophobic hydration for the apolar moieties. The waters of hydrophobic hydration, often referred to as clathrate or clathrate-like water, have specific thermodynamic properties: an exothermic heat of hydration (a negative $\Delta H$) and a negative entropy of hydration (6, 7). On raising the temperature, by means of an endothermic transition (8), the low entropy waters of hydrophobic hydration become bulk water with a significant increase in solvent entropy as the polymers fold and aggregate, optimizing intra- and intermolecular contacts between hydrophobic (apolar) moieties with a somewhat lesser decrease in polymer entropy than increase in solvent entropy. Such polymers, when their transitions occur between 0° and 100° C., can be used to control events in the aqueous environments that occur in biology.

The polypentapeptide poly($Val^1$-$Pro^2$-$Gly^3$-$Val^4$-$Gly^5$), also written poly(VPGVG), is a particularly well-balanced polymer for biological utilities as its transition is just complete near 37° C. Below 25° C., it is miscible with water in all proportions where it exhibits a β-turn (see structural formula above) in which there occur hydrogen bonds between the $Val^1$-CO and the $Val^4$-NH moieties (9). On raising the temperature, the polypentapeptide folds into a loose helix in which the dominant interturn hydrophobic contacts involve the $Val^1$-$\gamma CH_3$ moieties in one turn and the $Pro^2$-$\beta CH_2$ moiety in the adjacent turn (10). The loose helical structure is called a dynamic β-spiral and is proposed to be the basis for the entropic elastomeric force exhibited by this material once cross-linked (11). Concomitant with the folding is an assembly of β-spirals to form a twisted filament which optimizes intermolecular contacts.

When poly(VPGVG) is cross-linked, for example, by 20 Mrads of γ-irradiation, an elastomeric matrix is formed which is swollen below 25° C. but which on raising the temperature through the transition contracts with the extrusion of sufficient water to decrease the volume to one-tenth and to decrease the length of a strip of matrix to 45% of its swollen length (2). This thermally driven contraction has previously been used to lift weights that are one thousand times the dry weight of the matrix. This property is therefore called thermomechanical transduction. As will be discussed below, any chemical means of reversibility or irreversibility shifting the temperature of the transition can be used, isothermally, to achieve chemomechanical transduction and, as has just been discovered, to similarly modify the absorbent properties of the bioelastomers.

CHEMICAL MODULATION OF INVERSE TEMPERATURE TRANSITIONS AND ABSORBENCY: SELECTION OF BIOELASTOMERS

Figure 2:
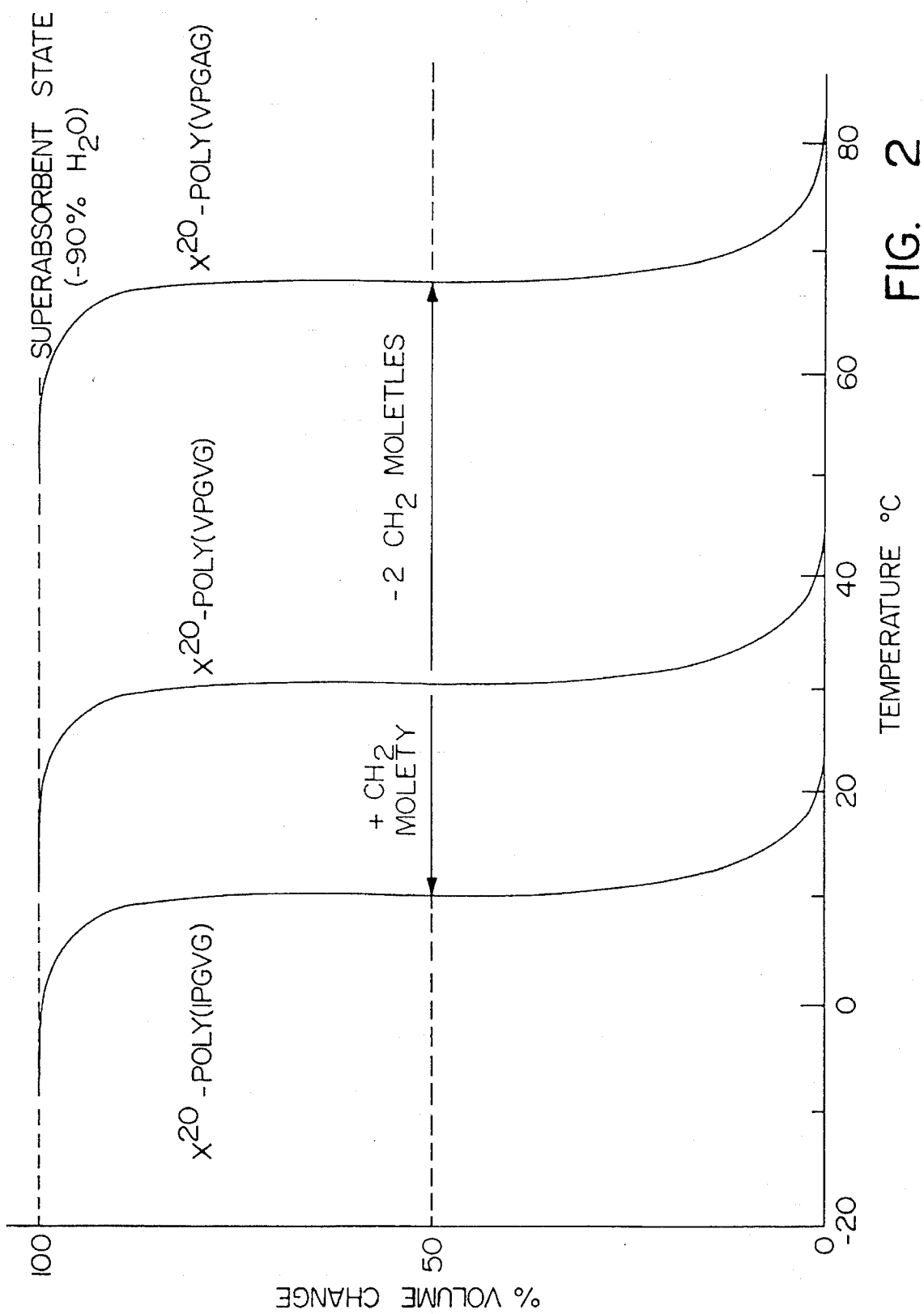
FIG. 2 is a graph showing modulation of inverse temperature transitions with variation in the polymer hydrophobicity.

The temperature of inverse temperature transitions can be changed by changing the hydrophobicity of the polymer. For example, make the polypeptide more hydrophobic, as with poly($Ile^1$-$Pro^2$-$Gly^3$-$Val^4$-$Gly^5$), where replacing $Val^1$ by $Ile^1$ represents the addition of one $CH_2$ moiety per pentamer, and the temperature of the transition decreases by 20° C. from 30° C. for poly(VPGVG) to 10° C. for poly(IPGVG) (1). Similarly, decreasing the hydrophobicity as by replacing $Val^4$ by $Ala^4$, i.e., removing the two $CH_2$ moieties per pentamer, and the temperature of the transition is raised by some 40° C. to 70° C. See FIG. 2, which shows this property graphically.

Figure 3:
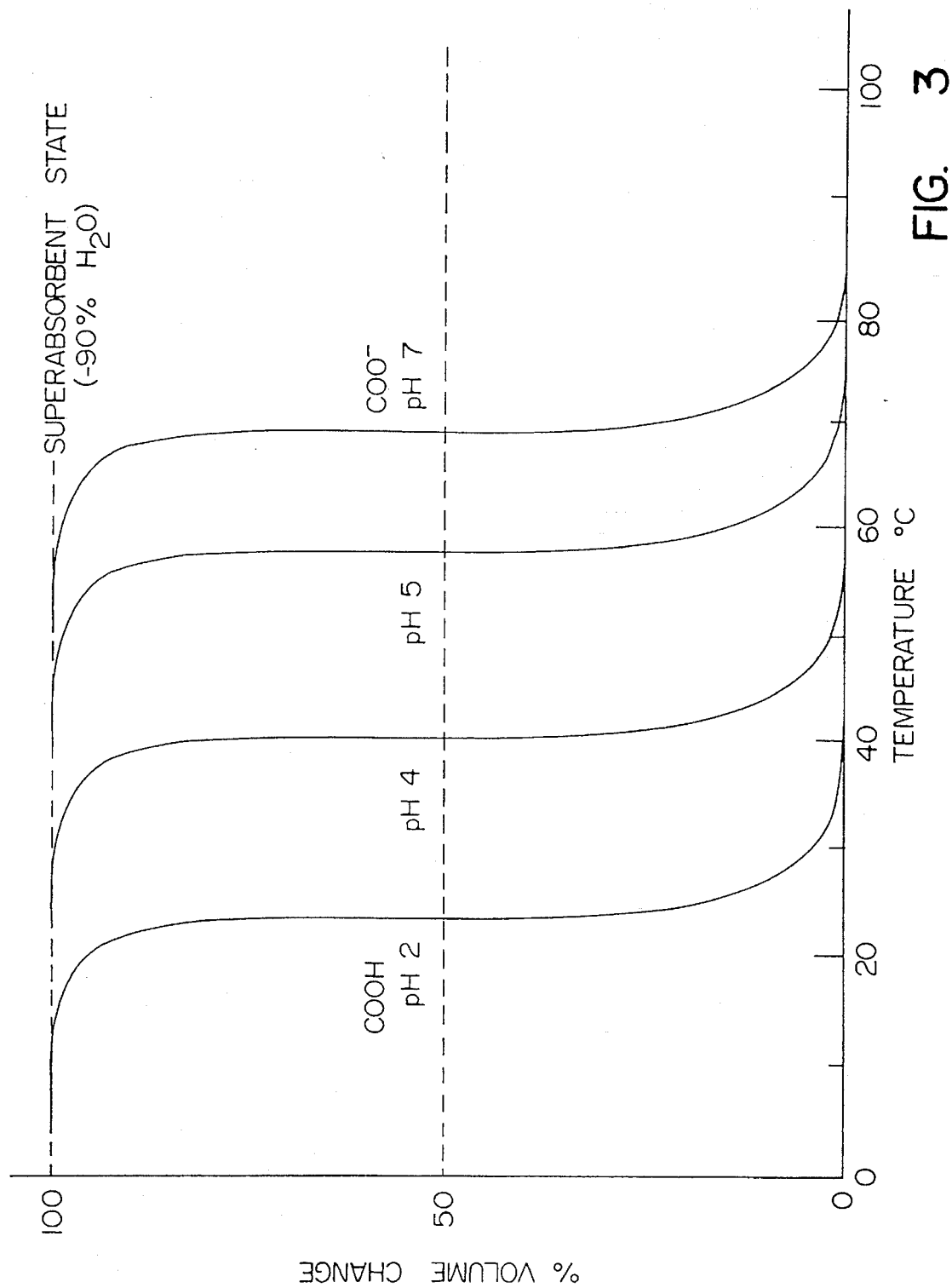
FIG. 3 is a graph showing modulation of inverse temperature transitions with changes in pH.

In terms of a generalized hydrophobicity scale, the COOH moiety is more hydrophobic than the $COO^-$ moiety such that by simply changing the pH of the environment contacting a bioelastomer with free carboxyl groups, the temperature of the transition can be changed. The transition temperature can be lowered by decreasing the pH and raised by increasing the pH when a carboxyl group is present (or other group capable of forming an ion upon increasing the pH). If an intermediate temperature is maintained, then a 20 Mrad cross-linked matrix of poly[4(VPGVG),(VPGEG)], that is, a random copolymer in which the two pentameric monomers are present in a 4:1 ratio, where E=Glu, will contract on lowering the pH and relax or swell on raising the pH (12). Alternatively, this formula can be written poly[0.8(VPGVG),0.2(VPGEG)], using a formulation that appears elsewhere in this specification. The temperature of the transition in phosphate buffered saline will shift some 50° C. from about 20° C. at low pH, giving COOH, to nearly 70° C. at neutral pH where all the carboxyls have been converted to carboxylate anions. See FIG. 3, which shows this property graphically.

For similarly cross-linked poly[4(IPGVG),(IPGEG)], the temperature of the inverse temperature transition shifts from near 10° C. for COOH to over 50° C. for $COO^-$ (5). For this more hydrophobic polypentapeptide, which contains 4 Glu residues per 100 total amino acid residues, it takes twice as many carboxylate anions to shift the transition to 40° C. as for the less hydrophobic polypentapeptide based on the VPGVG monomer. Thus, it is possible to change the conditions of the transition by varying the hydrophobicity of the region surrounding the group that undergoes the chemical change. Since contraction and relaxation of the bulk polymer is dependent on the sum of all local thermodynamic states, sufficient control is possible merely by controlling the average environment of, for example, ionizable groups, such as by changing the percentage of monomers present in a random (or organized) copolymer.

When the pH is lowered (that is, on raising the chemical potential, μ, of the protons present) at the isothermal condition of 37° C., these matrices can exert forces, $f$, sufficient to lift weights that are a thousand times their dry weight. This is chemomechanical transduction, also called mechanochemical coupling. The mechanism by which this occurs is called an hydration-mediated apolar-polar repulsion free energy and is characterized by the equation $(\delta\mu/\delta f)n<0$; that is, the change in chemical potential with respect to force at constant matrix composition is a negative quantity (13). Such matrices take up protons on stretching, i.e., stretching exposes more hydrophobic groups to water which makes the $COO^-$ moieties energetically less favored. This is quite distinct from the charge—charge repulsion mechanism for mechanochemical coupling of the type where $(\delta\mu/\delta f)n>0$; and where stretching of such matrices causes the release of protons. The hydration-mediated apolar-polar repulsion mechanism appears to be an order of magnitude more efficient in converting chemical work into mechanical work.

It may be emphasized here that any chemical means of changing the mean hydrophobicity of the polymer, such as an acid-base titrable function, dephosphorylation/phosphorylation, reduction/oxidation of a redox couple, etc., can be used to bring about contraction/relaxation. Most transitions will occur on the side chains of certain amino acids, preferably one of the 20 genetically encoded amino acids or a derivative thereof. Especially preferred are changes that can occur to genetically encoded amino acids as a result of contact with a physiological environment. Examples include ionization and neutralization of Glu, Asp, Lys, and His side chains; oxidation of the thio group of Cys (for example to form cystine) or reduction of an oxidized form to Cys; amidation of Glu or Asp; and deamidation of Gln or Asn. It is also possible to attach a moiety containing a functional group that undergoes a transition under conditions different from those attainable for naturally occurring amino acid side chains. For example, a sulfate ester of Ser can be prepared in which sulfate ionizations will occur at a pH outside the range experienced by carboxylate groups. A change in the oxidation state of NAD, a flavin, or a quinone attached to an amino acid by reaction of a functional group in the modifying moiety and a functional group in an amino acid side chain is also effective. A specific example of such a modified amino acid residue is a riboflavin attached to the carboxylate group of a Glu or Asp residue through formation of an ester linkage. Another example would be a heme moiety covalently bonded to the side chain of an amino acid. For example, protoporphyrin IX can be attached to the amino group of Lys through one of its own carboxylate groups. Heme A (from the cytochromes of class A) could be attached in a similar manner. Change in the oxidation state of, or coordination of a ligand with, the iron atom in a heme attached to an amino acid side chain can also be used to trigger the desired transition.

It is also possible to exert fine control over the transition from a relaxed to a contracted state (or vice versa) by controlling the average environment in which the various functional groups undergoing transition are located. For example, the hydrophobicity of the overall polymer (and therefore the average hydrophobicity of functional groups present in the polymer) can be modified by changing the ratio of different types of monomeric unit, as previously exemplified. These can be monomeric units containing the functional group undergoing the transition or other monomeric units present in the polymer. For example, if the basic monomeric unit is VPGVG and the unit undergoing transition is VPGKG, where K is a lysine residue, either the ratio of VPGVG unit to VPGKG units can be varied or a different structural unit, such as IPGVG, can be included in varied amounts until the appropriate transitions temperature is achieved.

In general, selection of the sequence of amino acids in a particular monomeric unit and selection of the required proportion of monomeric units can be accomplished by an empirical process that begins with determining (or looking up) the properties of known bioelastomers, making similar but different bioelastomers using the guidance provided in this specification, and measuring the transition temperature as described herein and in the cited patents and patent applications. Preferably, however, one uses tables of relative hydrophobicity of amino acid residues (either naturally occurring or modified) to compute the transition temperature without experimentation. For example, see Y. Nozaki and C. Tanford, *J. Biol. Chem.* (1971) 246:2211–2217, or H. B. Bull and K. Breese, *Archives Biochem. Biophys.* (1974) 161:665–670, for particularly useful compilations of hydrophobicity data. Some 30 different hydrophobicity scales exist, with the hydrophobicity scales that show tryptophan (Trp) as the most hydrophobic (or at least one of the most hydrophobic) residues being more appropriate for the practice of the present invention. For example, a rough estimate can be obtained of the likely transition temperature by summing the mean hydrophobicities of the individual amino acid residues in the monomeric units of the polymer and comparing the result to the sum obtained for polymers having known transition temperatures.

More accurate values can be calculated for any given polymer by measuring transition temperatures for a series of related polymers in which only one component is varied. For example, polymers that mostly contain VPGVG monomers with varying amounts of VPGKG monomers (e.g., 2%, 4%, and 8% K) can be prepared and tested for transition temperatures. The test merely consists of preparing the polymer in uncrosslinked form, dissolving the polymer in water, and raising the temperature of the solution until turbidity appears, which indicates the precipitation of polymer from solution. If the transition temperatures are plotted versus the fraction of VPGKG monomer in the polymer, a straight line is obtained, and the fraction of VPGKG necessary for any other desired temperature (within the limits indicated by 0% to 100% of the VPGKG monomer) can be obtained directly from the graph. When this technique is combined with the rough estimating ability of hydrophobicity summing as described above, any desired transition temperature in the range of liquid water can be obtained.

SELECTION OF BIOELASTOMERS THAT RESIST PRESSURE-DRIVEN EXPULSION OF LIQUIDS

It is also possible to provide absorbents of the invention in the form of a composition capable of resisting expulsion of retained water under the influence of an external pressure, comprising a bioelastic polymer containing elastomeric units selected from the group consisting of bioelastic pentapeptides, tetrapeptides, and nonapeptides, wherein at least a fraction of said elastomeric units contain at least one amino acid residue with a hydrophobic side chain in an amount sufficient to provide PdV/dS for said polymer of at least 0.2° K. The transition characteristics of the elastomers can be controlled by varying the hydrophobicity and size of the side chain (or side chains) and by varying the mole fraction of the hydrophobic units in the overall polymer.

It has been found that by including relatively large hydrophobic side chains in such polymers that the polymers will respond to pressure in an unexpected way. When pressure is increased on the polymers in an aqueous solution (or while the polymers are entrapping an aqueous medium), the polymers expand rather contract if additional bulk (non-associated) water is present. This property can be put to use to resist mechanical expulsion of absorbed water from absorbents of the invention, as described below.

For more information of the theoretical basis of this property of pressure resistance, see the application by the present inventor filed on even date with the present invention and entitled "Polymers Capable of Baromechanical and Barochemical Transduction" (Ser. No. 07/688,324, filed Apr. 22, 1991 now U.S. Pat. No. 5,226,292). This related application contains the first report on the effects of pressure on $T_t$ for poly(VPGVG) and its more sensitive analogues and describes how to use these systems to exhibit baromechanical transduction. High speed ultracentrifugation was used to develop increased pressures and an analytical ultracentrifuge was used to monitor the transition temperature. Several polymers were synthesized and studied including the homopolypentapeptides poly(GVGVP) and poly(GMGVP) and the complex polypentapeptides poly[0.8(GVGVP), 0.2(GYGVP)], poly[0.8(GVGVP),0.2(GFGVP)] and poly [0.857(GVGVP),0.143(GWGVP)] where M=Met, Y=Tyr, F=Phe, and W=Trp (listed in order of increasing pressure effect), and the results of those and other studies have lead to an understanding of how to design bioelastomers and other polymers used as absorbents to resist squeezing pressures.

Such polymers incorporate relatively large hydrophobic side chains into monomeric polypeptide units to produce a previously unrecognized property in the resulting overall polymer, namely a sensitivity of the inverse temperature transition of the polymer to external pressure. The new property is not strictly related to hydrophobicity in the same proportion as the temperature of the transition Tt, but requires the presence of large hydrophobic side chains. Here "large" means preferably larger in volume than an isopropyl group; i.e., larger than 20 cm$^3$/mole. Even larger hydrophobic groups are preferred (e.g., 100, 500, 1000, or even higher volumes as expressed in cm$^3$/mole). The hydrophobic groups are selected to be sufficiently large and to be present in sufficient extent to provide PdV/dS of at least 0.2° K, preferably at least 1° K, more preferably at least 5° K, and most preferably at least 20° K (where P=pressure, V=volume, and S=entropy). PdV/dS values can be experimentally determined by measuring changes in the inverse temperature transition for a given polymer with changes in pressure and plotting the temperature change versus the log of the pressure. The slope of the resulting line is PdV/dS. See the commonly filed application referenced above for a detailed experimental example of this process.

Examples of typical hydrophobic groups useful as side chains include butyl groups and larger hydrocarbons containing 4 or more carbon atoms. There is no particular limit on the upper size of the hydrocarbon other than the ability of the total polymer to undergo the desired inverse temperature transition, which can easily be determined experimentally. Preferred hydrocarbon groups contain 7 to 50 carbons, more preferably 7 to 20 carbons, and typically 7 to 15 carbons. A common substituent comprises a 6-member aromatic ring, such as a phenyl ring. Functional groups can be present on these hydrocarbons as long as the hydrophobic nature of the side chain as a whole is retained. Useful hydrophobicity scales for substituents are discussed in more detail below. When polypeptides are prepared, the amino acids phenylalanine, tryptophan, tyrosine, and histidine can be incorporated into the amino acid chains in order to provide the desired large hydrophobic side chains.

Either increasing the size of hydrophobicity of the hydrophobic groups present or increasing their amount (usually expressed as a mole fraction) in a polymer increases the PdV/dS value. However, knowledge of the exact PdV/dS value for a particular polymer is not required in order carry out the present invention, and estimates of whether any given polymer will be likely to have a desirable baromechanical or barochemical response can readily be made by comparison of the amount and type of hydrophobic groups present in a particular polymer. There are no particular upper limits on the size or amount of hydrophobic groups in a polymer of the invention or on the hydrophobicity of the particular substituent as long as the resulting polymer undergoes an inverse temperature transition and has the stated PdV/dS value. However, manufacturing is generally easier if water-soluble polymers (below the transition temperature) are used. Non-water-soluble polymers can be manufactured using organic solvents, but the organic solvent in most cases must be removed and replaced with water after forming the polymer matrix in order to achieve the results described herein.

The resistance to pressure is described initially using the model system that was originally helpful in determining the broader aspects of the invention that are later described herein. However, it will be recognized that this initial description is not limiting of the invention, as these examples can readily be modified using the later-described techniques to provide numerous compositions that have the properties discussed herein and which can be used in the methods and apparatuses described later.

The first polymer system showing the baromechanical properties described herein used elastic protein-based polymers of the formula poly[$f_x$(VPGXG),$f_v$(VPGVG)] where $f_x$ and $f_v$ are mole fractions with $f_x+f_v=1$. As described above, these bioelastomers exhibit inverse temperature transitions in the form of a phase separation in which folding and aggregation of water-soluble polymer chains into more-ordered states of the condensed (coacervate) phase occurs on raising the temperature. This inverse temperature transition, while uncommon in the universe of polymers, is common to the bioelastomers described herein and can readily be detected in other polymers by the simple solution/heating scheme described above. Investigations into the polymers of the formula immediately above in which X=Trp, Phe, or Tyr showed that an increase in pressure caused a substantial increase in the temperature of the transition such that an application of pressure when the polymer is above the transition temperature leads to unfolding and disaggregation of the polymer, such that the volume of the coacervate phase (or of a cross-linked matrix) increases on increasing pressure. Although the inventor does not intend to be limited by the theory of how this expansion takes place, it is believed that water molecules surrounding the aromatic side chains of Trp(W), Phe(F), or Tyr(Y) occupy less volume than water molecules in bulk water surrounding the polymer. The calculated volume change for poly[0.8(GVGVP),0.2(GFGVP)], for example, on going from coacervate phase where hydrophobic associations have largely eliminated waters of hydrophobic hydration to dispersed in water where the hydrophobic moieties are surrounded by water is 80 cm$^3$/mole of mean pentamers, or some 400 cm$^3$/mole of (GFGVP). The results provide the capacity to design materials capable of exhibiting baromechanical transduction.

It should be noted that the location of the "X" residue in the polymer as described above is not critical and was made in these examples principally for ease of synthesis, although some variations in properties do occur with substitution of other amino acid residues in the pentameric elastomer unit. However, the specific location of a side chain in the polymer is not important as long as the bulk properties of the polymer are maintained.

The effect of increased pressures on the temperature of inverse temperature transition, $T_t$, occurs but is quite unremarkable for poly(GVGVP) and poly(GMGVP). On the other hand, the pressure dependence of $T_t$ for polypentapeptides containing aromatic residues is striking. Making comparisons for the same extent of substitution at the same position within poly(Val$^1$-Pro$^2$-Gly$^3$-Val$^4$-Gly$^5$), the magnitude of the change in temperature of the transition, $\Delta T_t$, due to a given increase in pressure is 70 times greater for the Trp$^4$ and 60 times greater for the Phe$^4$ containing polypentapeptides than for the Val$^4$ containing polypentapeptide. Because of the different relative heats for the transitions (32), L=$\Delta H_t$, which are required to obtain an experimental evaluation of the entropies of the transition $\Delta S_t(=\Delta H_t/T_t)$, the calculated changes in volume for the transition, $\Delta V_t$, are somewhat different. From the slopes of the resulting plot versus log (or ln) P and with the values of $\Delta S_t$, the values for $\Delta V_t$, are obtained; the changes in volume are 100 times greater for the pentapeptides containing an aromatic residue at position four rather than the Val$^4$ residue. Significantly, the contracted state with respect to the inverse temperature transition for the cross-linked matrix (or of the coacervate) of the polypentapeptide is actually the state of increased volume for the system as a whole (i.e., the polymer and surrounding bulk water). This, of course, means that a gram of water of hydrophobic hydration occupies less volume than a gram of bulk water. The result is a useful effect in absorbents, since when pressure is applied to a molecular system capable of exhibiting an inverse temperature transition when the molecular system is at a temperature within the transition temperature range and when the composition is pressure sensitive, expulsion of liquids will be resisted as the composition attempts to hold on to, and in fact draw into the composition, adjoining bulk water (i.e., absorbed water in an absorbent).

The effect of pressure to increase the temperature of an inverse temperature transition has the important result in the transition temperature range of shifting the equilibrium for the polymer toward the swollen state, because this is the state for which the system as a whole and water in particular occupy the smaller volume. The coacervate phase for poly-(VPGVG) is 60% water and 40% peptide by weight at 37° C. (33). If, for example, the volume occupied by the 60% water is itself greater than the volume occupied by waters of hydrophobic hydration, then compression of the coacervate phase or of the cross-linked matrix in equilibrium with a water bath will produce a counter pressure due to the shift toward the low temperature, unfolded, swollen state in which an unfolding of the polypentapeptide would bring about exposure of hydrophobic residues with its more densely packed waters of hydrophobic hydration.

Figure 4:
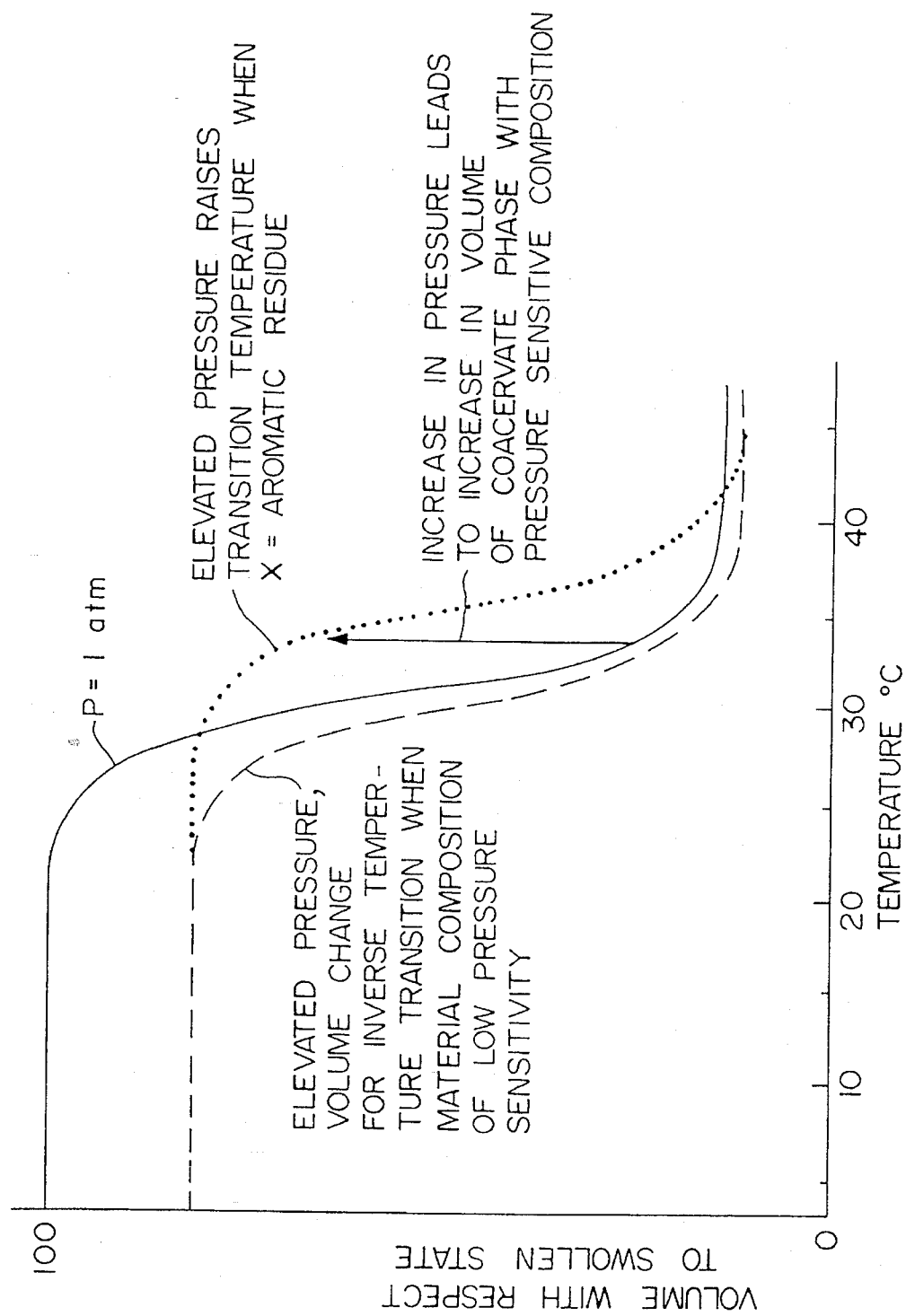
FIG. 4 is a graph showing resistance to pressure-driven expulsion of fluids from compositions of the invention.

This property is shown in FIG. 4, which contains plots of volume versus temperature. The solid curve is a plot of coacervate (or cross-linked matrix) volume versus temperature for a pressure of one atmosphere. Neglecting for the moment the unique pressure effects on an inverse temperature transition and taking the more swollen state to have a greater coefficient of compression than the contracted state gives the dashed curve or dotted curves (for two different polymers) for an elevated pressure. Since the effect of increased pressure is to increase the transition temperature, the result of a experimental 4° C. change in $T_t$ (e.g., for the Phe-containing polymer) at 30 atm would be the shift shown by the dotted curve. The effect of pressure is to shift the temperature of the inverse temperature transition in such a way as to counter the effect of applying the pressure.

Taking these experimental results into consideration, bioelastomers can be rationally designed in order to achieve the desired baromechanical properties described herein. The following discussion describes general selection techniques for achieving the results of the invention with a variety of different bioelastomers.

The discussions above relating in general to the phenomenon of controlling inverse temperature transitions in bioelastomers, regardless of whether those materials have the baromechanical and barochemical properties, is also relevant to varying the inverse temperature transition of compositions having pressure-sensitive properties. As previously discussed, polymers showing pressure sensitivity merely incorporate hydrophobic side chains of a sufficient number and size to provide the desired pressure-sensitive effects. Providing a polymer with the pressure-sensitive effects of the invention, however, does not eliminate the other properties of these polymers. Accordingly, it is possible to achieve the various mechanochemical and thermochemical properties that have been previously described in, for example, bioelastic materials by providing a polymer that contains functional groups in addition to those required for pressure sensitivity. A polymer will have the inherent thermal and mechanical properties (including absorbence) if it merely has the polymer backbone and the required inverse temperature transition. By providing large hydrophobic side chains, pressure capabilities will be provided, while providing side chains with chemical functionality will allow chemical interactions to take place.

The invention now being generally described, the same will be better understood by reference to the following examples, which are provided for purposes of illustration only and are not to be considered limiting of the invention unless so specified.

EXAMPLE

An absorbent appliance for use as a diaper can be constructed of paper fibers in the form of so-called fluff-pulp and bonding pulp such as those marketed under the trade name PULPEX by the American company Hercules. The bonding fibers will melt at their binding temperature and are bonded together with the subject absorbent thereby obtaining an absorption body which is comparatively shape-stable in both wet and dry states.

The surface of the appliance faces the user of the product and the opposing surface may be coated in a water-proof covering of plastic or other such material. The polymeric system can be formulated as a hydrogel or distributed in a fibrous web where the temperature gradient in the bulk dimension of the web can be varied.

Accordingly, the fluid penetrates into the diaper and through the absorbent material where the fluid is drawn to the superabsorbency of the cooler regions away from contact with the user and away from the generally warmer wetting point.

All publications and patent applications mentioned in this specification are herein incorporated by reference to the same extent as if each individual publication or patent application was specifically and individually indicated to be incorporated by reference at the location where cited.

The invention now being fully described, it will be apparent to one of ordinary skill in the art that many changes and modifications can be made thereto without departing from the spirit or scope of the appended claims.

What is claimed is:

1. In a method for absorbing an aqueous liquid with an absorbent, an improvement which comprises:

contacting said aqueous liquid with said absorbent, said absorbent comprising a dry bioelastic polymer comprising elastomeric units selected from the group consisting of bioelastic pentapeptides, tetrapeptides, and nonapeptides, and absorbing said liquid with said dry bioelastic polymer, thereby producing a wet bioelastic polymer.

2. The method of claim 1, wherein said aqueous liquid is an ink, paint, or dye.

3. The method of claim 1, wherein said liquid is sweat, urine, or blood.

4. The method of claim 1, wherein said liquid is ink, paint, or dye and said polymer is coated on a transfer roller.

5. The method claim 1, wherein said liquid is a bulk spill and said polymer is in the form of a powder.

6. The method of claim 1, wherein said dry bioelastic polymer undergoes an inverse temperature transistion at a pre-selected temperature, wherein said dry bioelastic polymer is selected to be in a contracted, less absorbent state at a temperature higher than said pre-selected temperature and in a swollen, more absorbent state when at a temperature lower than said pre-selected temperature.

7. The method of claim 1, wherein said elastomeric unit is a pentapeptide.

8. The method of claim 1, wherein said elastomeric unit is a tetrapeptide.

9. The method of claim 1, wherein said elastomeric unit is a nonapeptide.

10. The method of claim 1, wherein said elastomeric unit comprises a VPGVG repeating unit.

11. The method of claim 1, wherein said absorbent is a diaper.

12. The method of claim 1, wherein said absorbent is a hygenic device selected from the group consisting of sanitary pads, tampons and sweat pads.

13. The method of claim 1, wherein said absorbent is a medical device selected from the group consisting of bandages, wound dressings, medical sponges, and swabs.

14. The method of claim 1, wherein said absorbent is a sanitary device selected from the group consisting of tissues, napkins, catbox liners, toilet paper, towelettes and cleaning wipes.

15. In a method for absorbing an aqueous liquid with an absorbent, an improvement which comprises:

contacting said aqueous liquid with said absorbent comprising a polymeric material that undergoes an inverse temperature transition, and absorbing said liquid with said polymeric material, thereby producing a wet polymeric material.

* * * * *